United States Patent
Wurtman et al.

(10) Patent No.: US 6,579,899 B1
(45) Date of Patent: Jun. 17, 2003

(54) COMPOSITION FOR TREATMENT OF STRESS

(75) Inventors: Judith J. Wurtman, Boston, MA (US); Richard J. Wurtman, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/492,110

(22) Filed: Jan. 27, 2000

Related U.S. Application Data

(63) Continuation-in-part of application No. 09/354,738, filed on Jul. 16, 1999, now abandoned.
(60) Provisional application No. 60/093,013, filed on Jul. 16, 1998.

(51) Int. Cl.[7] ...................... A61K 31/405; A61K 31/41; A61K 31/497; A61K 31/51; A61K 31/137
(52) U.S. Cl. .................. 514/419; 514/383; 514/252.15; 514/275; 514/221; 514/649
(58) Field of Search .......................... 424/330; 514/419, 514/383, 252.15, 275, 221, 649

(56) References Cited

U.S. PATENT DOCUMENTS

| | | | |
|---|---|---|---|
| 3,198,834 A | 8/1965 | Beregi et al. | 260/570.8 |
| 4,309,445 A | 1/1982 | Wurtman et al. | 424/325 |
| 4,452,815 A * | 6/1984 | Wurtman et al. | 514/654 |
| 5,283,263 A | 2/1994 | Norden | 514/651 |
| 5,502,080 A | 3/1996 | Hitzig | |
| 5,561,149 A | 10/1996 | Azria et al. | |
| 5,597,826 A | 1/1997 | Howard et al. | |
| 5,658,955 A * | 8/1997 | Hitzig | 514/654 |
| 5,716,976 A * | 2/1998 | Bernstein | 514/386 |
| 5,852,020 A | 12/1998 | Marcus et al. | |
| 5,885,976 A * | 3/1999 | Sandyk | 514/159 |
| 5,916,923 A | 6/1999 | Rudolph et al. | |

FOREIGN PATENT DOCUMENTS

| | | |
|---|---|---|
| EP | 0 654 264 A1 | 11/1994 |
| FR | 2710916 | 4/1995 |
| WO | WO93/16695 | 9/1993 |

OTHER PUBLICATIONS

Mathus–Vliegen et al., Dexfenfluramine in the treatment of severe ovesity: a placebo–controlled investigation of the effects on weight loss, cardiovascular risk factors, food intake and eating behaviour, 1992, J. of Int. Med., Vol. 232, pp. 119–127.*
Mathus–Vliegen et al. Dexfenfluramine in the treatment of severe obesity: a placebo–controlled investigation of the effects on weight–loss, cardiovascular risk factors, food intake and eating behaviour, 1992, Journal of Internal Medicine, vol. 232 pp. 119–127.*
Goodman and Gilman's *Pharmacological Basis of Therapeutics*, Seventh Edition, 1985, Alfred G. Gilman et al., editors, pp. 192–201.

Dexfenfluramine: Effects on Food Intake in Various Animal Models, Neil E. Rowland and Janis Carlton, *Clinical Neuropharmacology*, vol 11, suppl. 1, pp. S33–S50, 1988.
Wurtman et al., *Science*, vol. 198, pp. 1178–1180, Dec., 1977.
Abstract for "Treatment of Post–Traumatic Stress Syndrome".
Abstract for "Metabolic and hormonal effects of dexfenfluramine on stress situations,".
Zethof et al., "Stress–induced hyperthermia as a putative anxiety model," *European Journal of Pharmacology*, 294 (1995), pp. 125–135.
Papp et al., "Pharmacological validation of the chornic mild stress model of depression," *European Journal of Pharmacology*, 296 (1996), pp. 129–136.
McKittrick et al., "Serotonin Receptor Binding in a Colony Model of Chronic Social Stress," *Biological Psychiatry*, 1995; vol. 37, pp. 383–393.
Graeff et al., "Role of 5–HT in Stress, Anxiety, and Depression," *Pharmacology Biochemistry and Behavior*, (1996) vol. 54, No. 1, pp. 129–141.
Neal et al., "An open trial of moclobemide in the treatment of post–traumatic stress disorder," *International Clinical Psychopharmacology* (1997), vol. 12, pp. 231–237.
Davidson, "Biological Therapies of Posttraumatic Stress Disorder: An Overview," *J. Clin. Psychiatry*, 1997, vol. 58 (supp. 9), pp. 29–32.
Friedman, "Drug Treatment for PTSD: Answers and Questions," National Center for PTSD, White River Junction, VT and Depts. of Psychiatry and Pharmacology: Dartmouth Med. School, Hanover, NH, XP–000914298, pp. 359–371.
Abstract XP–002197787.
Abstract XP–002197788.
Abstract XP–002197789.
Wurtman et al., "Fenfluramine and Fluoxetine Spare Protein Consumption While Suppressing Caloric Intake by Rats," *Science: American Association for the Advancement of Science*, Dec. 1977, vol. 198, No. 4322.
Rowland et al., "Dexfenfluramine: Effects on Food Intake in Various Animal Models," *Clinical Neuropharmacology*, vol. 11, Supplement 1, 1988, pp. S33–S50.
Wurtman et al., "Brain Serotonin, Carbohydrate–Craving, Obesity and Depression," *Journal of Obesity Research*, vol. 3, Supp. 4, Nov. 1995, pp. 477S–480S.
Radloff, "The CES–D Scale: A Self–Report Depression Scale for Research in the General Population," *Applied Psychological Measurement*, vol. 1, No. 3 Summer 1997, pp. 385–401.

* cited by examiner

*Primary Examiner*—Frederick Krass
*Assistant Examiner*—Donna Jagoe
(74) *Attorney, Agent, or Firm*—Gilberto M. Villacorta; Serge Sira; Katten Muchin Zavis Rosenman

(57) ABSTRACT

A method of treating stress in a patient showing stress related symptoms is disclosed, where the method comprises administering to the patient an effective amount of a serotoninergic drug or prodrug. Specific examples of such drugs are described, and include, among others, tryptophan or 5-hydroxytryptophan, or their salts.

28 Claims, No Drawings

COMPOSITION FOR TREATMENT OF STRESS

RELATED APPLICATIONS

The present application is a continuation-in-part of U.S. application Ser. No. 09/354,738, filed Jul. 16, 1999, now abandoned which claims priority from U.S. provisional application Ser. No. 60/093,013, filed Jul. 16, 1998, each of which is incorporated herein by reference in its respective entirety.

GOVERNMENT SUPPORT

The present invention was made with government support under Grant Number NIH-5M01-RR00088, awarded by the National Institutes of Health. The government has certain rights in the invention.

FIELD OF THE INVENTION

The invention relates to a novel process for treating stress in a subject suffering from at least one symptom of stress. More specifically, the invention relates to the use of precursors or prodrugs that enhance serotonin-mediated neurotransmission, as well as intermediates in the biosynthesis of serotonin, for treating stress in such a subject.

BACKGROUND OF THE INVENTION

Individuals responding to stressful events can experience one, two or three of the following stages: (1) stage one, mobilization of energy; (2) stage two, exhaustion or consuming energy; and (3) stage three, draining energy stores.

In stage one, the mobilization of energy, the body responds to stress through a release of Adrenalin and a fight or flight response. Symptoms of this stage include increased heart rate and blood pressure, rapid breathing, sweating, decreased digestion rate and indigestion.

If there is no relief from stage one, the individual enters phase two, exhaustion or consuming energy. Here, the body will begin to release stored sugars and use up fats. Symptoms of this stage include feeling driven, feeling pressured, tiredness and fatigue, increased smoking, coffee drinking and/or alcohol consumption, anxiety, memory loss, and acute illnesses such as colds and flu.

If either the stressful situation is not resolved, or the individual's reaction to the situation is not changed, the individual enters phase three, draining energy sources. Here, the individual becomes chronically stressed, and the body's need for energy resources outpaces its ability to produce them. Symptoms of this stage include serious illnesses such as heart disease, ulcers, and mental illness, as well as insomnia, errors in judgment, and personality changes.

At present, patients suffering from stress related disorders are treated for the symptoms of stress by the use of pharmaceutical compositions containing drugs such as anxiolytics or sometimes with beta-blockers. Anxiolytics frequently used include drugs such as benzodiazepines, diazepam being a specific example. The beta-blocking drugs used for treatment of such patients include propranolol. The use of these classes of drugs for such treatments is discussed in *Goodman and Gilman's Pharmacological Basis of Therapeutics*, Seventh Edition, 1985, Alfred G. Gilman et al., editors, pages 192–201, the entirety of which is herein incorporated by reference.

The serotoninergic drug fenfluramine is known to be an effective drug for treating obesity. The racemic mixture, D,L-fenfluramine, is disclosed in U.S. Pat. No. 4,452,815 as being effective for inhibiting the abnormal craving for carbohydrates which afflicts some people and is associated with obesity. Dexfenfluramine is also indicated for use in treating patients who cannot control their eating habits or appetite. The use of dexfenfluramine for this purpose was disclosed in U.S. Pat. No. 4,309,445. In both of these patents, fenfluramines were used for treating a patient's appetite or craving for certain types of food. Nowhere in these patents is the use of fenfluramines taught or suggested for treatment of stress or stress symptoms.

Wurtman, et al., in Brain Serotonin, Carbohydrate-Craving, Obesity and Depression, *Obesity Research*, vol. 3, suppl. 4, Nov. 4, 1995, pages 477S–480S present a theoretical mechanism by which fenfluramines work for suppressing appetite for certain food types, the entirety of which is herein incorporated by reference. Dexfenfluramine is shown in this publication to be useful for treating obesity suffered by such people, but there is no teaching or suggestion that dexfenfluramine is useful for treating stress itself.

Wurtman et al. describes the serotoninergic fenfluramines as acting to facilitate weight loss in subjects in three ways:

"They accelerate the onset of satiety and enhance basal metabolic rate by about 100 calories per day. They also inhibit the 'carbohydrate craving' manifested by many people who are overweight or are becoming so, and there is reason to believe that this inappropriate eating behavior actually constitutes a 'serotonin hunger' by the brain, in which case giving the serotoninergic drug might constitute a specific therapy for the etiologic process causing the obesity."

Further discussion of the known functioning of fenfluramines is found in Wurtman, et al., Brain Serotonin, Carbohydrate-Craving, Obesity and Depression, *Recent Advances in Tryptophan Research*, G. A. Filippini, et al. eds., Plenum Press, New York, 1996, pages 35–41 the entirety of which is herein incorporated by reference.

The use of dexfenfluramine for treating animals inflicted with periodic pain is discussed in Dexfenfluramine: Effects on Food Intake in Various Animal Models, Rowland, et al., *Clinical Neuropharmacology*, vol. 11, suppl. 1, pp. S33–S50 the entirety of which is herein incorporated by reference. This article indicates in the abstract that: ". . . both stress-induced eating as well as a food-motivated response (running) are particularly sensitive to inhibition by dexfenfluramine."

Rowland et al. discloses the administration of dexfenfluramine to rats exhibiting increased eating behavior in response to tail pinching. Dexfenfluramine (DF) was found to decrease the eating behavior of the tail pinched rats.

Rowland, et al., discusses the implications of their experiments with regard to stress-induced eating as follows on page S37, wherein DF refers to dexfenfluramine:

"Mild tail pressure induces eating and gnawing in rats, and this may be a model of stress-induced eating in humans. Garattini reported that DF potently inhibits tail pressure-induced eating, and that the $DI_{50}$ of 0.6 mg/kg is about one-half of the doses effective in the other paradigms reviewed so far. It was previously reported that racemic fenfluramine inhibits tail pressure-induced eating as well as concurrent behaviors such as gnawing, locomotion, and vocalization. In the study with DF, only the amount eaten was reported, rather than all oral behaviors. These data thus suggest that DF may be an especially potent inhibitor of stress-related eating. Further studies are needed to clarify the effect of DF on other oral behaviors, as well as whether it has 'anti-stress' effects along with its anorectic action."

Rowland, et al., indicate only that fenfluramines inhibit tail pinching-induced eating and other behaviors stemming from the tail pinching protocol in rats. Rowland, et al. did not teach or suggest that fenfluramines can be used as a treatment for reducing stress itself. Thus, until the present invention, it was only known that dexfenfluramine inhibits eating in rats which have had their tails pinched. It was not previously known whether dexfenfluramine or d,1-fenfluramine in particular, or serotoninergic drugs in general, would be effective for treatment of stress. One skilled in the art would not have been led by the results of Rowland, et al. in rats, to treat humans suffering from stress with dexfenfluramine.

A need continues to exist for improved and alternative methods and compositions for treating stress and symptoms related thereto.

SUMMARY OF THE INVENTION

Briefly, the present invention is a novel treatment for stress and symptoms of stress in a subject. The applicants have discovered that administering precursors or prodrugs that enhance serotonin-mediated neurotransmission to a patient in need thereof can bring about a reduction in the stress felt by the patient and the symptoms of stress manifested by the patient. The treatment of stress and stress related symptoms of a patient with the compounds of the present invention has not been previously reported.

The present invention provides an appropriate treatment for stress in human patients, especially those suffering from stress-induced overeating. This invention is based on the discovery that prodrugs of serotonin, or intermediates in the biosynthesis of serotonin, such as tryptophan or 5-hydroxytryptophan, or their salts, can alleviate symptoms of stress in patients, when administered in effective amounts or at appropriate dosages.

Accordingly, the present invention is directed to a method of treating a human subject exhibiting one or more symptoms of stress, which comprises administering to the subject an effective amount of a compound which enhances serotonin-mediated neurotransmission such as d,1-fenfluramine or dexfenfluramine, or a pharmaceutically acceptable salt thereof. In a specific embodiment of the invention, when the fenfluramine is d,1-fenfluramine or a pharmaceutically acceptable salt thereof, an effective dose ranges from about 15 to about 150 mg/day, preferably from about 40 to about 80 mg/day. When the fenfluramine is dexfenfluramine or a pharmaceutically acceptable salt thereof, an effective dose ranges from about 5 to about 150 mg/day, preferably from about 15 to about 45 mg/day.

The present invention is further directed to a method of treating a human subject exhibiting one or more symptoms of stress, which comprises administering to the subject an effective amount of a precursor or prodrug that enhances serotonin-mediated neurotransmission, such as tryptophan or 5-hydroxytryptophan, or a pharmaceutically acceptable salt thereof. In a specific embodiment of the invention, when either tryptophan or 5-hydroxytryptophan or a pharmaceutically acceptable salt thereof is administered, an effective dose ranges from about 20 mg to about 4 g/day, preferably from about 50 mg to about 1 g/day, more preferably about 50 mg to about 400 mg/day, and most preferably about 100 mg/day.

According to the present invention, a treatment is provided which results in a reduction in the stress level of the patient experiencing emotional and other kinds of stress.

Accordingly, it is an object of the invention to provide a treatment for stress and symptoms related thereto.

It is another object of the invention to provide a treatment for stress which is also useful for controlling food intake in a either a stress-induced overeating patient or a stress-induced undereating patient.

It is another object of the invention to provide a treatment for non-eating related stress symptoms of a patient including but not limited to increased blood sugar in the diabetic patient, fatigue, insomnia, depression, high blood pressure, headaches, digestive changes, neck pain, back ache, tension, anxiety, anger, obsessive thinking reclusiveness, pessimism, increased irritability, inability to concentrate, inability to perform at ones previous level, and the like.

It is another object of the invention to provide a treatment for stress in a patient, wherein the treatment is with a drug other than an anxiolytic or beta-blocking drug.

Other objects will become apparent from the description of the invention which follows.

DETAILED DESCRIPTION OF THE INVENTION

Stress is classified by convention as being either acute or chronic in nature. A patient suffering from a stress related disorder can exhibit a variety of types of symptoms. These symptoms can include increased blood sugar in the diabetic patient, fatigue, insomnia, depression, high blood pressure, headaches, digestive changes, neck pain, back ache, tension, anxiety, anger, sadness, impairment of self esteem, reclusiveness, pessimism, increased irritability, inability to concentrate, inability to perform at ones previous level, obsessive thinking overeating, under eating, and the like. Disclosed herein is a novel treatment method for stress in a patient, which method uses drugs hitherto unknown as useful for treating stress. The novel method disclosed herein provides a useful method for treating patients suffering from stress and exhibiting at least one symptom thereof. In a specific embodiment of the invention, said method has been found particularly useful for treating stress felt by subjects who also suffer from overeating disorders or who overeat in reaction to the stress that they are experiencing.

The method and agents of the invention are also used to treat normal patients, that is, patients with no overt symptoms of stress. Thus the methods of the invention are used prophylactically to prevent, delay, diminish, or attenuate the onset of stress and stress-related symptoms. The methods disclosed herein are used for people who have been, or will soon be, exposed to a stressful environment or situation, but before onset of increased heart rate, rapid breathing, sweating, decreased digestion, or indigestion.

The applicants' experiments have now permitted the discovery that such antistress effects can be achieved with serotoninergic drugs in general and 5-hydroxytryptophan in particular.

According to the present invention, a novel method for treating stress comprises the administration of stimulators of serotonin-mediated neurotransmission, to a patient with stress related symptoms. In a preferred embodiment, the method comprises the administration of effective amounts of either tryptophan or 5-hydroxytryptophan, or their salts.

Drugs that reduce the effects of stress in a patient might not necessarily be useful in all obese patients. Some people who overeat respond to stress by reducing their eating, not increasing their eating behavior. According to the present invention, the stress reducing drugs that prove to be the most useful for weight reduction are those that elicit in patients, whose overeating is stress associated, a response that leads to a reduction in their eating behavior. Similarly, the stress reducing drugs that prove to be the most useful for weight gain are those that elicit in patients, whose under eating is stress associated, a response that leads to a gain in their eating behavior A number of compounds stimulate or enhance serotonin-mediated neurotransmission, sometimes referred to as serotoninergic drugs, and are thus useful in treating humans with one or more symptoms of stress. These compounds include the following: D,L-fenfluramine, dexfenfluramine, tryptophan, lithium, chlorimipramine, cyanimipramine, fluoxetine, paroxetine, fluvoxamine, citalopram, femoxitine, cianopramine, sertraline, sibutramine, venlafaxine, ORG 6582, RU 25591, LM 5008, DU 24565, indalpine, CGP 6085/A, WY 25093, alaprociate, zimelidine, trazodone, amitriptyline, imipramine, trimipramine, doxepin, protriptyline, nortriptyline, dibenzoxazepine, deprenyl, isocarboxazide, phenelzine, tranylcypromine, furazolidone, procarbazine, moclobemide, brofaromin, nefazodone, bupropion, MK 212, DOI, m-CPP, Ro 60-0175/ORG 35030, Ro 60-0332/ORG 35035, Ro 60-0175, Org 12962, Ro 60-0332, α-methyl-5-HT, TFMPP, bufotenin, Ru 24969, quipazine, 5-carboxyamidotryptamine, sumatriptan, CGS 12066, 8-OH-DPAT, (S)-2-(chloro-5-fluoro-indol-1-yl)-1-methylethylamine 1:1 C4H404, (S)-2-(4,4,7-trimethyl-1,4-dihydro-indeno(1,2-b)pyrrol-1-yl)-1-methylethylamine 1:1 C4H404, SB 206553, and pharmaceutically acceptable salts thereof. Suitable salts can be formed from the above compounds, for example, as addition salts using the following acids: inorganic acids such as hydrochloric acid, sulfuric acid, and phosphoric acid or organic acids such as acetic acid, maleic acid, valeric acid, caproic acid, benzoic acid and nicotinic acid.

"Fenfluramines" is used in the present application as meaning a racemic mixture of D,L-fenfluramine, which is also called N-ethyl-α-methyl-3-(trifluoro-methyl) benzeneethanamine; the dextrorotatory isomer known as dexfenfluramine and also as D-fenfluramine; or the pharmaceutically acceptable salts of these compounds. Suitable salts can be formed from dexfenfluramine or D,L-fenfluramine, for example, as addition salts using the following acids: inorganic acids such as hydrochloric acid, sulfuric acid, and phosphoric acid or organic acids such as acetic acid, maleic acid, valeric acid, caproic acid, benzoic acid and nicotinic acid.

The serotoninergic drugs MK-212, DOI, m-CPP, Ro 60-0175/ORG 35030, Ro 60-0332/ORG 35035, Ro 60-0175, Org 12962, Ro 60-0332, (S)-2-(chloro-5-fluoro-indol-1-yl)-1-methylethylamine 1:1 C4H404, (S)-2-(4,4,7-trimethyl-1,4-dihydro-indeno(1, 2-b)pyrrol-1-yl)-1-methylethylamine 1:1 C4H404, and SB 206553 fall into the class of drugs which activate postsynaptic receptors. These are agonist drugs which bombard the serotonin receptors of postsynaptic cells and mimic the effect of large amounts of serotonin reacting with the postsynaptic cells' serotonin receptors. Examples of the use of three of these drugs along with the chemical names and sources thereof are shown in EXAMPLES 13–15.

6-Chloro-2-(1-piperazinyl)pyrazine (MK-212), can be obtained from Merck & Co., Inc. Whitehouse Station, N.J. (S)-2-(4, 4, 7-trimethyl-1, 4-dihydro-indeno (1, 2-B) pyrrol-1-yl-)-1-methyl-ethylamine (Ro 60-175/ORG 35030) can be obtained from F. Hoffmann-LaRoche Ltd., Basel, Switzerland. (S)-2-(Chloro-5-fluoro-indol-1-yl)-1-methylethylamine (Ro 60-0332/ORG 35035) is obtained from F. Hoffmann LaRoche Ltd., Basel, Switzerland. 1-(2, 5-dimethoxy-4-iodophenyl)-2-aminopropane (DOI) can be obtained from Research Biochemical International, Natick, Mass. 1-(3-Chlorophenyl)piperazine (m-CPP) can be obtained from Research Biochemical International, Natick, Mass.

Other drugs, preferably halogenated amphetamines, can also be useful to treat stress in a subject. Such other useful drugs can include specific drugs that are not halogenated amphetamines including, but not limited to, effexor, nefazodone, bupropion, paroxetine, fluoxetine, and sertralin.

Because serotonin present in the bloodstream is excluded by the blood-brain barrier from entry into the brain, the administration of precursors such as L-tryptophan (L-TP) or L-5-hydroxytryptophan (L-5-HTP) is used to increase brain concentrations of serotonin (Wurtman and Fernstrom (1975) "Control of brain monoamine synthesis by diet and plasma amino acids." The American Journal of Clinical Nutrition, 28, 638–647), incorporated herein by reference in its entirety. The daily supplementation of precursors for serotonin comprises administering, for an effective daily period, an effective amount of L-tryptophan or preferably L-5-hydroxytryptophan as the intermediate precursors for serotonin (5-hydroxytryptamine). It is understood that any of its L, D or racemic forms are suitable, but preferably precursors are in L form. Furthermore, one skilled in the art will know to make tryptophan from 3-indolacetic acid or 3-indolpyruvic acid or use these acids as alternative to tryptophan and thus avoid the hepatic degradation by tryptophan pyrrolase. Other precursors or intermediates thereof are equally suitable with or without further modification, including but not limited to diethyl N-benzyloxycarbonyl-5-benzyloxycarbonyloxy-L-tryptophyl-L-aspartate, dibenzyl N-benzyloxycarbonyl-5-hydroxy-L-tryptophanylaspartate, 5-Hydroxy-L-tryptophyl-L-aspartic acid trihydrate, diethyl N-benzyloxycarbonyl-5-hydroxy-L-tryptophyl-L-glutamate, diethyl 5-hydroxy-L-tryptophyl-L-glutamate hydrochloride, dibenzyl L-benzyloxycarbonyl-5-hydroxytryptophyl-L-glutamate, 5-hydroxy-L-tryptophyl-L-glutamic acid, pentachlorophenyl ester of N-benzyloxycarbonyl-5-hydroxy-L-tryptophan, methyl ester of N-benzyloxycarbonyl-5-hydroxy-L-tryptophyl-L-tyrosine, N-Acetyl-5-hydroxy-L-tryptophan, methyl ester of N-acetyl-5-hydroxy-L-tryptophyl-L-tyrosine, methyl ester of n-acetyl-5-hydroxy-L-tryptophyl-5-hydroxy-L-tryptophan, 5-hydroxy-L-tryptophyl-L-alanine hydrate, 5-hydroxy-L-tryptophan-L-valine, 5-hydroxy-L-tryptophyl-L-leucine, 5-hydroxy-L-tryptophyl-L-proline, 5-hydroxy-L-tryptophyl-L-phenylalanine, 5-hydroxy-L-tryptophyl-5-hydroxy-L-tryptophan, 5-hydroxy-L-tryptophyl-L-tryptophan, 1-5-hydroxytryptophyl-L-serine, 5-hydroxy-L-tryptophyl-L-arginine, 5-hydroxy-L-tryptophylglycine, 5-hydroxy 1-tryptophyl-gamma-aminobutyric acid, 5-hydroxy-L-tryptophanamide hydrate, methyl ester of 5-hydroxy-L-tryptophyl-L-histidine, benzyl ester of L-5-hydroxytryptophan, benzyl ester of N-benzyloxycarbonyl-5-hydroxy-L-tryptophyl-5-hydroxy-L-tryptophan, 5-Hydroxy-L-tryptophyl-5-hydroxy-L-tryptophan hemihydrate, 5-hydroxytryptophan inosinate, theophylline salt of (DL) 5-hydroxytryptophan, and the like.

These serotonin precursors can be administered alone or in combination with the stimulants of serotonin synthesis including but not limited to vitamin B1, vitamin B3, vitamin B6, biotin, S-adenosylmethionine, folic acid, ascorbic acid, magnesium, coenzyme Q10, and piracetam.

Alternatively and additionally one skilled in the art will know to include serotoninergic drugs that act as serotonin agonists including but not limited to ergolide mesylate, pergolide mesylate, buspirone, (3 beta)-2,3-dihydrolysergine, (3 beta)-2,3-dihydroisolysergine, (3 beta)-

2,3-dihydrolysergol, (3 beta)-2,3-dihydrolysergene, (3 beta, 5 beta, 8 beta)-9,10-didehydro-2,3-dihydro-6-methyl-8-(methylthiomethyl) ergoline, (3 beta, 5 beta, 8 beta)-9,10-didehydro-2,3-dihydro-6-methylergoline-8-ac etonitrile, (3 beta, 5 beta, 8 beta)-9,10-didehydro-2,3-dihydro-6-methyl-8-(phenylthiomethyl) ergoline, (3 beta, 5 beta, 8 beta)-9,10-didehydro-2,3-dihydro-6-methyl-8-(2-pyridyl thiomethyl) ergoline, (3 beta)-2,3-dihydro-methyllysergate, (3 beta, 5 beta, 8 beta)-9,10-didehydro-2,3-dihydro-8-methyl-6-propylergoline.

For practicing the invention, the active serotonin-mediated neurotransmission stimulating compound can be administered to a patient as a pharmaceutical composition comprising the active compound admixed with a pharmaceutically acceptable carrier, including one or more excipients. For example, the compound or precursor can be administered to a patient as a pharmaceutical composition comprising in a preferred embodiment either L-tryptophan or L-5-hydroxytryptophan admixed with a pharmaceutically acceptable carrier, including one or more excipients.

It is to be understood that according to the teachings of the invention, the invention can be practiced by administering serotonin-mediated neurotransmission stimulating compounds, for example, tryptophan or 5-hydroxytryptophan, to a subject as a single unit dose one or more times per day, or as a plurality of unit doses once or more times per day without deviating from the teachings of the invention.

It is to be further understood that the present invention as disclosed herein, also includes a method of making a medicament for treating stress, wherein the method comprises a step of mixing a serotonin precursor such as tryptophan or 5-hydroxytryptophan with a pharmaceutically acceptable inert ingredient.

For the purposes of this disclosure, the terms "subject" and "patient" are used interchangeably to refer to a human exhibiting at least one symptom of stress.

The pharmaceutically acceptable carrier, excipient, and/or inert ingredient of choice utilized for a formulation used in accordance with the invention depends on the mode of administration to a subject. The compositions of this invention are suitable for oral, parenteral, buccal, sublingual or rectal administration. The resulting pharmaceutical compositions are, for example, tablets, coated tablets, capsules, soft gelatin capsules, drinkable emulsions, suspensions or solutions for oral or injectable administration, sublingual tablets or suppositories. They can also be formulated into a sustained release form. Among the various excipients which can be used for these purposes include talc, magnesium phosphate, lactose or silica or the like. To the solid forms can be added a filler, a diluent, a binder such as ethyl-cellulose, dihydroxypropyl cellulose, carboxymethyl cellulose, microcrystalline cellulose, gum arabic, gum tragacanth or gelatin. The compositions of this invention can also be flavored, colored or coated with a wax or a plasticizer.

The compositions of this invention can also be administered through sachets to which the subject adds water, or as a food based preparation, functional food, dietary supplement or nutraceutical. For the purposes of this application, "functional food" is defined as a food engineered or supplemented to give improved nutritional value, "dietary supplement" is defined as a substance produced by isolation, or microbial culture purification that gives health benefits, and "nutraceutical" is defined as a food, or parts of a food, that provide medical or health benefits, including prevention and treatment of clinical conditions and/or symptoms related thereto. The compositions of this invention can also be isolated from varying plants or components thereof including but not limited to root, tuber, rind/peel, bark, seed, fruit, bulb, flower, rhizome, leaf, stem, oil, shell, capsule, twig, resin, extract, and bean. In addition, the aforementioned components can be consumed by the subject, thereby providing the subject with the active ingredient(s) of the invention disclosed herein.

It is to be understood that those skilled in the art of pharmaceutical formulation will be able to make a variety of formulations that would be within the scope of this disclosure and the appended claims, without departing from the spirit and teachings of the invention. It is intended that all such formulations be included in this invention.

The invention will now be described through illustrative examples. The examples are not intended to limit the scope of the invention, which is limited only by the appended claims.

EXAMPLES

A subgroup of obese individuals is identified, which individuals describe themselves as being unable to control their eating and who attempt to continue on a weight-reducing diet when experiencing emotional distress. These patients are treated for four months by enrolling them in a weight loss program which includes the administration of dexfenfluramine at 30 mg/day and which involves adherence to a reduced-calorie meal plan. The use of dexfenfluramine is found to enhance the ability of stressed overeaters to lose weight.

As used herein, the Body Mass Index (BMI) is defined as the weight in kilograms of a subject, divided by the subject's height in meters squared.

A survey is conducted of 189 women of normal body weight (Body Mass Index <25, average Body Mass Index 22.5±0.36), who are not put on the weight-reduction regimen, and 211 obese women (Body Mass Index>25, average Body Mass Index 38.1±0.39). Of these obese women, 50 are entered into the weight loss program. The majority of the obese women responding to the survey report that emotional distress or other types of stress significantly increase their snack intakes and their cravings for sweet and starchy foods. Also, stress clearly decreases their ability to control their food intake and to adhere to a weight-loss regimen. In contrast, the majority of the normal weight women responding to the survey report no alterations in eating behavior when experiencing emotional distress or other stresses. Most obese respondents identify anxiety, depression, exhaustion, boredom, anger, tension, frustration, sadness, and impairment of self-esteem as the stress-induced emotions or symptoms most likely to make them unable to control their food intake. The kinds of stresses that the patients indicate produce these emotions or symptoms include, among others, family and job problems, boredom, unresolved emotional conflicts and bad news.

Objective measurements of emotional distress are made in some patients using the CES-D (Center for Environmental Studies Depression Form) test, which measures current levels of emotional distress (Radloff, et al., *The CES-D Scale: A Self Report Depression Scale for Research in the General Population* Applied Psychological Measurement 1: 385–401, 1977); and the POMS (Profile of Mood States test, that assesses tension, depression, anger and confusion (McNair, et al., *Profile of Mood States Manual*;San Diego: Educational and Industrial Testing Service, 1971); both of these references are hereby incorporated by reference in their entirety. These tests are also given monthly during the treatment period. At the same time, patients also complete questionnaires that ask the patients to rate their appetite and hunger, and also to rate their tendency to eat in response to a variety of emotional and stressful triggers. The patients are also weighed monthly.

The obese, stressed patients receiving dexfenfluramine exhibit a weight loss of 12±1.8 pounds (5.45±0.82 kg) during the four month study period. Six women receiving dexfenflurarnine, whose CES-D scores are above normal at the start of the study, also exhibit a lowered CES-D score. Scores are lowered from 34 to 7, 37 to 8, 22 to 9, 19 to 5, 15 to 7, and 15 to 3, respectively, for these six women. The mean group score, which at the beginning of the study is 9.4, fluctuates between 7 and 8 throughout the treatment period.

Scores on the appetite and stress-induced overeating scales are also reduced compared with baseline levels. The initial score on the appetite and hunger scale is 10.5, which decreased to 5.0 during the treatment period. The summed Tension, Depression, Anger and Confusion scores on the POMS test at baseline is 24. This number dropped to 16.8 during the study period. Moreover, the score on the emotional triggers to overeating report dropped from 23.4±9.8 to 8.6±8.5 standard deviations by the end of the treatment period.

Hence, treatment with a fenfluramine such as dexfenfluramine, specifically promotes the ability to control food intake and to lose weight among stress-induced overeaters. More surprisingly, treatment reduces the indicators of stress in these patients.

In order to confirm the relationship between drugs which enhance serotonin-mediated neurotransmission and the amelioration of symptoms and consequences of stress, i.e. overeating and obesity, a number of serotoninergic drugs are tested on overweight patients using the above protocols.

Specific examples of the results that are obtained with drugs that enhance serotonin-mediated neurotransmission are provided below.

EXAMPLE 1

Example 1 involves treatment with D,L-fenfluramine at 30 mg/day. A preferred dosage is about 5 mg/day to about 150 mg/day.

C. B. is a 48 year old white single female. She states in her screening forms that when she is upset or stressed she snacks on chocolate, popcorn, crackers, pretzels, and candy. She notes that she overeats when feeling frustrated, overwhelmed, and lonely and writes in answer to a question about whether she has difficulty in sticking to a diet when upset or stressed: "In the past when I am not in a formalized program, somehow my brain thinks I'm given a license to graze to placate my emotions when stressed. I tend to break all my own 'house' rules and eat anything I want."

The results are shown below in Table 1. Her starting weight is 216 pounds (98.2 kg) and after 4 months on dexfenfluramine, she drops to 205.5 pounds (93.4 kg). Her baseline CES-D Mood Scores drops from 5 to 1 over the treatment period, and her emotional triggers decrease from a baseline of 23 to a value of 4 after four months. Hence, the treatment also greatly relieves her emotional distress.

TABLE 1

|  | Baseline | Month 1 | Month 2 | Month 3 | Month 4 |
| --- | --- | --- | --- | --- | --- |
| Mood Scores CES-D | 5 | 1 | 3 | 2 | 1 |
| Appetite and Cravings | 10 | 2 | 5 | 5 | 4 |
| Emotional Triggers | 23 | 2 | 3 | 2 | 4 |

EXAMPLE 2

Example 2 involves treatment with dexfenfluramine hydrochloride at 30 mg/day. A preferred dosage range is from about 15 mg/day to about 45 mg/day.

C. M. is a 46 year old white married physician and mother of two. She reports in her initial screening report that when stressed, she snacks on chocolate, candy, chips, cookies, cake/pie, and popcorn. She writes: "I was on Weight Watchers, doing well even during vacation. But upon the start of the school year with all the schedules to handle, I was unable to keep with the program. Then the Christmas holidays were upon us and I was working really hard at the office. I started gaining weight and I could not stop eating. My appetite has tripled and it is hard for me to say no."

The results are shown in Table 2 below. Her starting weight is 198 pounds (90.0 kg) and at the end of 4 months on dexfenfluramine, her weight drops to 181.7 pounds (82.6 kg). Her baseline CES-D Mood Scores drops from 19 to 4 over the treatment period, and her emotional triggers decrease from a baseline of 30 to a value of 7 after four months. Hence, the treatment also greatly relieves this patient's stress levels.

TABLE 2

|  | Baseline | Month 1 | Month 2 | Month 3 | Month 4 |
| --- | --- | --- | --- | --- | --- |
| Mood Scores CES-D | 19 | 5 | 2 | 3 | 4 |
| Appetite and Cravings | 9 | 6 | 8 | 3 | 5 |
| Emotional Triggers | 30 | 12 | 13 | 5 | 7 |

EXAMPLE 3

Example 3 involves the treatment of a 57 year old married female with lithium carbonate at 900 mg/day for four months. A preferred dose is about 600 mg/day to about 1500 mg/day.

D. R. states in her screening forms that when she is upset or stressed she overeats on beer and crabs, as well as snack food such as potato chips and peanuts. This occurs when she feels stress or frustration from her employment as a government lawyer.

The results are shown below in Table 3. Her starting weight is 246 pounds (111.8 kg) and after 4 months on lithium drops to 225 pounds (102.3 kg). Her baseline CES-D Mood Scores drops from 4 to 2 over the treatment period, and her emotional triggers decrease from a baseline of 15 to a value of 7 after four months. Hence, the treatment also greatly relieves her emotional distress and stress.

TABLE 3

|  | Baseline | Month 1 | Month 2 | Month 3 | Month 4 |
|---|---|---|---|---|---|
| Mood Scores CES-D | 4 | 3 | 3 | 2 | 2 |
| Appetite and Cravings | 14 | 6 | 9 | 5 | 3 |
| Emotional Triggers | 15 | 16 | 10 | 6 | 7 |

EXAMPLE 4

Example 4 involves the treatment of a 35 year old single white female with fluoxetine hydrochloride at a dose from 20 mg/day for the first two weeks, 40 mg/day the second two weeks, 60 mg/day the third two weeks, and 80 mg/day through the end of the four month trial. The preferred dose is about 10 mg/day to about 160 mg/day.

The results are shown below in Table 4. T. M. reports in her initial screening report that when stressed, she chronically overeats at meals, although she eats nothing between and after meals. Her overeating takes the form of non-stop eating, consuming a loaf of bread and a stick of butter at a single meal. Her starting weight is 183 pounds (83.2 kg) and at the end of 4 months on fluoxetine hydrochloride, her weight drops to 172 pounds (78.2 kg). Her baseline CES-D Mood Scores drops from 15 to 7 over the treatment period, and her emotional triggers decrease from a baseline of 31 to a value of 12 after four months. Hence, the treatment also greatly relieves this patient's stress levels.

TABLE 4

|  | Baseline | Month 1 | Month 2 | Month 3 | Month 4 |
|---|---|---|---|---|---|
| Mood Scores CES-D | 15 | 10 | 2 | 6 | 7 |
| Appetite and Cravings | 17 | 6 | 9 | 3 | 4 |
| Emotional Triggers | 31 | 22 | 13 | 10 | 12 |

EXAMPLE 5

Example 5 involves the treatment of a 76 year old single white female with fluvoxamine maleate at a dose from 50 mg/day for the first week, 100 mg/day the second week, and 150 mg/day through the end of the four month trial. The preferred dose is about 25 mg/day to about 300 mg/day.

J. B. complains of feelings of stress associated with social activities in the retirement community in which she lives. While clearly overweight, she does not complain about weight nor apparently recognizes her condition.

The results are shown in Table 5 below. Her starting weight is 302 pounds (137.3 kg) and after 4 months on dexfenfluramine, drops to 286 pounds (130 kg). Her baseline CES-D Mood Scores drops from 23 to 17 over the treatment period, and her emotional triggers decrease from a baseline of 34 to a value of 24 after four months. The treatment relieves her social stress and has the additional benefit of modest weight reduction.

TABLE 5

|  | Baseline | Month 1 | Month 2 | Month 3 | Month 4 |
|---|---|---|---|---|---|
| Mood Scores CES-D | 23 | 26 | 16 | 15 | 17 |
| Appetite and Cravings | 18 | 16 | 11 | 12 | 14 |
| Emotional Triggers | 34 | 27 | 30 | 20 | 24 |

EXAMPLE 6

Example 6 involves the treatment of a 42 year old married white female with sertraline hydrochloride at a dose from 50 mg/day for the first week, 100 mg/day the second week, and 200 mg/day through the end of the four month trial. The preferred dose is about 25 mg/day to about 400 mg/day.

P. Q. is employed as an accountant, has two small children, and experiences stress during the tax season. She eats between meals and reports wakening at night with anxiety which is relieved by consumption of ice cream.

The results are shown in Table 6 below. Her starting weight is 173 pounds (78.6 kg) and at the end of 4 months on sertraline, her weight drops to 160 pounds (72.7 kg). Her baseline CES-D Mood Scores drops from 20 to 12 over the treatment period, and her emotional triggers decrease from a baseline of 22 to a value of 3 after four months. Hence, the treatment relieves both the stress levels and the overweight.

TABLE 6

|  | Baseline | Month 1 | Month 2 | Month 3 | Month 4 |
|---|---|---|---|---|---|
| Mood Scores CES-D | 20 | 16 | 16 | 10 | 12 |
| Appetite and Cravings | 15 | 12 | 5 | 3 | 1 |
| Emotional Triggers | 22 | 12 | 13 | 5 | 3 |

EXAMPLE 7

Example 7 involves the treatment of a 38 year old single white female with venlafaxine hydrochloride at a dose from 75 mg/day for the first week, 100 mg/day the second week, and 150 mg/day through the end of the four month trial. The preferred dose is about 50 mg/day to about 300 mg/day.

L. Z., a single mother of four children, operates a day care center in her home and complains of continual stress. She eats baked goods excessively in the evening after the children have gone home or to bed.

The results are shown below in Table 7. Her starting weight is 184 pounds (83.6 kg) and after 4 months on dexfenfluramine, drops to 169 pounds (76.8 kg). Her baseline CES-D Mood Scores drops from 8 to 2 over the treatment period, and her emotional triggers decrease from a baseline of 14 to a value of 2 after four months. Hence, the treatment also greatly relieves her emotional distress.

TABLE 7

|  | Baseline | Month 1 | Month 2 | Month 3 | Month 4 |
|---|---|---|---|---|---|
| Mood Scores CES-D | 8 | 4 | 6 | 2 | 2 |

TABLE 7-continued

|  | Baseline | Month 1 | Month 2 | Month 3 | Month 4 |
|---|---|---|---|---|---|
| Appetite and Cravings | 10 | 6 | 7 | 3 | 1 |
| Emotional Triggers | 14 | 9 | 4 | 6 | 2 |

EXAMPLE 8

Example 8 involves the treatment of a 44 year old single white female with amitriptyline hydrochloride at a dose from 75 mg/day for the first week, to 100 mg/day through the end of the four month trial. The preferred dose is about 50 mg/day to about 200 mg/day.

E. E. reports stress from her employment as a dispatcher for a trucking company. Her discomfort is relieved by eating fried foods, especially fried potatoes.

The results are shown in Table 8 below. Her starting weight is 198 pounds (90.0 kg) and at the end of 4 months on dexfenfluramine, her weight drops to 182 pounds (82.6 kg). Her baseline CES-D Mood Scores drop from 29 to 18 over the treatment period, and her emotional triggers decrease from a baseline of 25 to a value of 3 after four months. Hence, the treatment also greatly relieves this patient's stress levels.

TABLE 8

|  | Baseline | Month 1 | Month 2 | Month 3 | Month 4 |
|---|---|---|---|---|---|
| Mood Scores CES-D | 29 | 22 | 20 | 23 | 18 |
| Appetite and Cravings | 19 | 16 | 8 | 13 | 8 |
| Emotional Triggers | 25 | 22 | 13 | 5 | 3 |

EXAMPLE 9

Example 9 involves the treatment of a 30 year old married white female with trazodone hydrochloride at a dose of 100 mg/day in divided doses of 50 mg each through the end of the four month trial. The preferred dose is about 50 mg/day to about 200 mg/day.

N. J., with three small children, reports an unhappy and stressful home life with an interfering mother-in-law and ineffectual husband. Her stress seems relieved by late-night snacking on sweet food.

The results are shown in Table 9 below. Her starting weight is 203 pounds (92.3 kg) and at the end of 4 months on sertraline, her weight drops to 160 pounds (72.7 kg). Her baseline CES-D Mood Scores drops from 9 to 1 over the treatment period, and her emotional triggers decrease from a baseline of 12 to a value of 3 after four months. Hence, the treatment relieves both the stress level and the weight problem.

TABLE 9

|  | Baseline | Month 1 | Month 2 | Month 3 | Month 4 |
|---|---|---|---|---|---|
| Mood Scores CES-D | 9 | 16 | 16 | 10 | 1 |
| Appetite and Cravings | 9 | 5 | 5 | 3 | 5 |

TABLE 9-continued

|  | Baseline | Month 1 | Month 2 | Month 3 | Month 4 |
|---|---|---|---|---|---|
| Emotional Triggers | 12 | 12 | 9 | 5 | 3 |

EXAMPLE 10

Example 10 involves the treatment of a 31 year old married white female with imipramine hydrochloride at an intramuscular dose of 75 mg/day through the end of the four month trial. The preferred dose is about 50 mg/day to about 150 mg/day.

A. R., is employed at a consulting engineering firm and attends law school at night. Her regimented schedule and lack of exercise may contribute to her feelings of stress, which engenders over-eating.

The results are shown below in Table 10. Her starting weight is 163 pounds (74.1 kg) and after 4 months on imipramine, drops to 155 pounds (70.4 kg). Her baseline CES-D Mood Scores drops from 36 to 20 over the treatment period, and her emotional triggers decrease from a baseline of 22 to a value of 8 after four months. Hence, the treatment also greatly relieves her emotional distress.

TABLE 10

|  | Baseline | Month 1 | Month 2 | Month 3 | Month 4 |
|---|---|---|---|---|---|
| Mood Scores CES-D | 36 | 34 | 26 | 21 | 20 |
| Appetite and Cravings | 15 | 12 | 7 | 3 | 6 |
| Emotional Triggers | 22 | 15 | 14 | 6 | 8 |

EXAMPLE 11

Example 11 involves the treatment of a married 42 year old white female with trimipramine maleate at a dose from 75 mg/day for the first week, to 100 mg/day through the end of the four month trial. The preferred dose is about 50 mg/day to about 200 mg/day.

A. B., a teacher in a metropolitan school, reports stress which she attributes to her work and generally unhappy home life. She is unable to control episodic binge eating of ice cream and cake.

The results are shown in Table 11 below. Her starting weight is 180 pounds (81.8 kg) and at the end of 4 months on trimipramine, her weight drops to 158 pounds (71.8 kg). Her baseline CES-D Mood Scores drops from 25 to 13 over the treatment period, and her emotional triggers decrease from a baseline of 14 to a value of 3 after four months. Hence, the treatment also greatly relieves this patient's stress levels.

TABLE 11

|  | Baseline | Month 1 | Month 2 | Month 3 | Month 4 |
|---|---|---|---|---|---|
| Mood Scores CES-D | 25 | 22 | 20 | 15 | 13 |
| Appetite and Cravings | 11 | 9 | 8 | 13 | 6 |
| Emotional Triggers | 14 | 8 | 13 | 6 | 3 |

EXAMPLE 12

Example 12 involves the treatment of a single 50 year old white female with phenelzine sulfate at a dose from 45 mg/day for the first week, to 60 mg/day through the end of the four month trial, each daily dose taken in three portions. The preferred dose is about 15 mg/day to about 120 mg/day.

D. C. is a suburban bus driver and finds driving in traffic stressful. She constantly diets but is unable to successfully lose weight.

The results are shown in Table 12 below. Her starting weight is 184 pounds (83.6 kg) and at the end of 4 months on phenelzine, her weight drops to 174 pounds (79.1 kg). Her baseline CES-D Mood Scores drops from 20 to 14 over the treatment period, and her emotional triggers decrease from a baseline of 20 to a value of 7 after four months. Hence, the treatment also greatly relieves this patient's stress levels.

TABLE 12

|  | Baseline | Month 1 | Month 2 | Month 3 | Month 4 |
|---|---|---|---|---|---|
| Mood Scores CES-D | 20 | 22 | 20 | 15 | 14 |
| Appetite and Cravings | 19 | 15 | 8 | 13 | 12 |
| Emotional Triggers | 20 | 8 | 13 | 6 | 7 |

EXAMPLE 13

The effect of the hydrochloride salt of 6-chloro-2-(1-piperazinyl)pyrazine (MK-212, which is obtained from Merck & Co., Inc. Whitehouse Station, N.J.), on stress related eating in animals is determined through the observation of the effect of experimental compounds on stress-related eating in adult Sprague-Dawley rats. These rats are widely used as a recognized animal model useful in predicting the effect of serotoninergic drugs in humans.

In these experiments, a group of 5 adult female and 5 adult male Sprague-Dawley rats weighing between 200 and 250 grams each are used as control animals. An untightened clamp is placed on the tail of these animals. The untightened clamp provides the unstressed condition. Each animal is placed in an individual cage and allowed free access to food. The amount of food consumed is determined at 2, 4 and 8 hours after the initiation of the trial. A similar group of rats has a clamp tightened on the tail. The amount of food consumed by this stressed group of rats is shown in the 0 mg/kg column. Three similar groups of stressed rats are injected with 1, 2, 5, or 10 mg/kg body weight of MK-212 one hour before initiation of the experiment.

The results are shown in Table 13 below. The average amount of food in mg which is consumed per rat 8 hours after initiation of the trials is shown in the following table. The relative amounts of stress eating with the amount at 0 mg/kg MK-212 as 100% is also shown in the Stress Eating row. The preferred daily dose of MK-212 is about 1 mg/kg body weight to about 10 mg/kg body weight.

Table 13 shows that MK-212 reduces stress-related eating which indicates that the administration of MK-212 reduces stress.

TABLE 13

| MK-212 | 0 mg/kg | 1 mg/kg | 2 mg/kg | 5 mg/kg | 10 mg/kg |
|---|---|---|---|---|---|
| Control Rats | 1.25 | 1.32 | 1.20 | 1.16 | 1.03 |
| Stressed Rats | 4.63 | 4.14 | 3.78 | 2.01 | 0.97 |
| Stress Eating | 3.38 (100%) | 2.82 (83%) | 2.58 (76%) | 0.85 (25%) | 0.0 (0%) |

EXAMPLE 14

Example 14 shows the effect of (S)-2-(4, 4, 7-trimethyl-1, 4-dihydro-indol (1, 2-B) pyrrol-1-yl)-1-methylethylamine (Ro 60-175/ORG 35030) which is obtained from F. Hoffmann-LaRoche Ltd., Basel, Switzerland, on stress-induced eating. The experiment is done as in Example 13 and Table 13 except that Ro 60-175/ORG 35030 is used instead of MK-212. The preferred daily dose of Ro 60-175/ORG 35030 is about 1 mg/kg body weight to about 10 mg/kg body weight.

Table 14 below shows that Ro 60-175/ORG 35030 reduces stress related eating which indicates that the administration of Ro 60-175/ORG 35030 reduces stress.

TABLE 14

| Ro 60-175/ ORG 35030 | 0 mg/kg | 1 mg/kg | 2 mg/kg | 5 mg/kg | 10 mg/kg |
|---|---|---|---|---|---|
| Control Rats | 1.31 | 1.28 | 1.30 | 1.20 | 1.13 |
| Stressed Rats | 4.51 | 3.66 | 1.43 | 1.30 | 1.16 |
| Stress Eating | 3.20 (100%) | 2.38 (74%) | 0.13 (4%) | 0.10 (3%) | 0.03 (1%) |

EXAMPLE 15

The effect of (S)-2-(Chloro-5-fluoro-indol-1-yl)-1-methylethylamine (Ro 60-0332/ORG 35035) which is obtained from F. Hoffmann LaRoche Ltd., Basel, Switzerland, on eating in stressed rats is determined as in EXAMPLE 13 and Table 13, except Ro 60-0332/ORG 35035 is used rather than MK-212. The preferred daily dose of Ro 60-0332/ORG 35035 is about 1 mg/kg body weight to about 10 mg/kg body weight.

Table 15 below shows that Ro 60-0332/ORG 35035 reduces stress-related eating which indicates that the administration of Ro 60-0332/ORG 35035 reduces stress.

TABLE 15

| Ro 60-0332/ ORG 35035 | 0 mg/kg | 1 mg/kg | 2 mg/kg | 5 mg/kg | 10 mg/kg |
|---|---|---|---|---|---|
| Control Rats | 1.23 | 1.29 | 1.20 | 1.21 | 1.28 |
| Stressed Rats | 4.72 | 4.87 | 2.19 | 1.83 | 1.74 |
| Stress Eating | 3.49 (100%) | 3.58 (103%) | 0.99 (28%) | 0.60 (17%) | 0.46 (13%) |

EXAMPLE 16

A patient experiencing stress induced insomnia is treated with an effective amount of serotonin precursors and/or intermediates in the form of a nutraceutical. The patient experiences reduced feelings of stress including a reduction in her insomnia.

EXAMPLE 17

A diabetic patient experiencing stress induced increased blood sugar is treated with an effective amount of serotonin precursors and/or intermediates in the form of a dietary supplement and in conjunction with a multivitamin. The patient experiences reduced blood sugar levels.

EXAMPLE 18

A patient experiencing stress induced fatigue is treated with an effective amount of L-tryptophan in the form of a functional food and in conjunction with a stimulant of serotonin synthesis. The patient experiences reduced fatigue and describes herself as feeling alert.

EXAMPLE 19

A patient experiencing stress induced depression is treated with an effective amount of L-5-hydroxytryptophan in the form of a food based preparation and in conjunction with a serotoninergic drug which acts as a serotonin agonist. The patient experiences reduced depression, and both her baseline CES-D Mood Score and emotional triggers score drops over the treatment period. Hence, the treatment also relieves her emotional distress.

EXAMPLE 20

A patient experiencing stress induced high blood pressure is treated with an effective amount of L-5-hydroxytryptophan in conjunction with a stimulant of serotonin synthesis. The patient experiences decreased stress and lower blood pressure.

EXAMPLE 21

A patient experiencing stress induced headaches is treated with an effective amount of serotonin precursors and/or intermediates in the form of a dietary supplement and in conjunction with a multivitamin. The patient experiences decreased stress and a reduction in the frequency and severity of headaches.

EXAMPLE 22

A patient experiencing stress induced neck and back pain is treated with an effective amount of L-tryptophan in the form of a functional food and in conjunction with a stimulant of serotonin synthesis. The patient experiences reduced stress as indicated by his CES-D Mood Score and emotional triggers score. The patient also reports reduced back and neck pain.

EXAMPLE 23

A patient experiencing stress induced inability to concentrate is treated with an effective amount of L-5-hydroxytryptophan in the form of a food based preparation. The patient experiences improved concentration, and both her baseline CES-D Mood Score and emotional triggers score drops over the treatment period. Hence, the treatment also relieves her stress.

While the invention has been described herein with reference to specific and preferred embodiments, it is understood that changes, modifications, substitutions and omissions may be made without departing from the spirit and scope of the invention, which is limited only by the appended claims.

What is claimed is:

1. A method of treating a human subject suffering from or experiencing stress and exhibiting at least one symptom thereof, comprising administering to said subject an effective amount of a compound, which is a precursor or prodrug of serotonin, or an intermediate in the biosynthesis of serotonin, or a pharmaceutically acceptable salt thereof.

2. The method of claim 1, wherein the compound or a pharmaceutically acceptable salt thereof is administered at a dose ranging from about 20 mg/day to about 4 g/day.

3. The method of claim 2 in which the compound or pharmaceutically acceptable salt thereof is administered at a dose ranging from about 50 mg/day to about 1 g/day.

4. The method of claim 1, wherein the compound is selected from the group consisting of L-tryptophan, L-5-hydroxytryptophan, diethyl N-benzyloxycarbonyl-5-benzyloxycarbonyloxy-L-tryptophyl-L-aspartate, dibenzyl N-benzyloxycarbonyl-5-hydroxy-L-tryptophanylaspartate, 5-Hydroxy-L-tryptophyl-L-aspartic acid trihydrate, diethyl N-benzyloxycarbonyl-5-hydroxy-L-tryptophyl-L-glutamate, diethyl 5-hydroxy-L-tryptophyl-L-glutamate hydrochloride, dibenzyl L-benzyloxycarbonyl-5-hydroxytryptophyl-L-glutamate, 5-hydroxy-L-tryptophyl-L-glutamic acid, pentachlorophenyl ester of N-benzyloxycarbonyl-5-hydroxy-L-tryptophan, methyl ester of N-benzyloxycarbonyl-5-hydroxy-L-tryptophyl-L-tyrosine, N-Acetyl-5-hydroxy-L-tryptophan, methyl ester of N-acetyl-5-hydroxy-L-tryptophyl-L-tyrosine, methyl ester of n-acetyl-5-hydroxy-L-tryptophyl-5-hydroxy-L-tryptophan, 5-hydroxy-L-tryptophyl-L-alanine hydrate, 5-hydroxy-L-tryptophan-L-valine, 5-hydroxy-L-tryptophyl-L-leucine, 5-hydroxy-L-tryptophyl-L-proline, 5-hydroxy-L-tryptophyl-L-phenylalanine, 5-hydroxy-L-tryptophyl-5-hydroxy-L-tryptophan, 5-hydroxy-L-tryptophyl-L-tryptophan, 1-5-hydroxytryptophyl-L-serine, 5-hydroxy-L-tryptophyl-L-arginine, 5-hydroxy-L-tryptophylglycine, 5-hydroxy 1-tryptophyl-gamma-aminobutyric acid, 5-hydroxy-L-tryptophanamide hydrate, methyl ester of 5-hydroxy-L-tryptophyl-L-histidine, benzyl ester of L-5-hydroxytryptophan, benzyl ester of N-benzyloxycarbonyl-5-hydroxy-L-tryptophyl-5-hydroxy-L-tryptophan, 5-Hydroxy-L-tryptophyl-5-hydroxy-L-tryptophan hemihydrate, 5-hydroxytryptophan inosinate, theophylline salt of (DL) 5-hydroxytryptophan, and combinations thereof.

5. The method of claim 4, wherein the compound is administered in combination with a stimulant of serotonin synthesis selected from the group consisting of vitamin B1, vitamin B3, vitamin B6, biotin, S-adenosylmethionine, folic acid, ascorbic acid, magnesium, coenzyme Q10, piracetam and combinations thereof.

6. The method of claim 4, wherein the compound is administered in combination with an agent selected from the group consisting of ergolide mesylate, pergolide mesylate, buspirone, (3beta)-2,3-dihydrolysergine, (3beta)-2,3-dihydroisolysergine, (3beta)-2,3-dihydrolysergol, (3beta)-2,3-dihydrolysergene, (3beta, 5beta, 8beta)-9,10-didehydro-2,3-dihydro-6-methyl-8-(methylthiomethyl) ergoline, (3beta, 5beta, 8beta)-9,10-didehydro-2,3-dihydro-6-methylergoline-8-acetonitrile, (3beta, 5beta, 8beta)-9,10-didehydro-2,3-dihydro-6-methyl-8-(phenylthiomethyl) ergoline, (3beta, 5beta, 8beta)-9,10-didehydro-2,3-dihydro-6-methyl-8-(2-pyridyl thiomethyl) ergoline, (3beta)-2,3-dihydro-methyllysergate, (3beta, 5beta, 8beta)-9,10-didehydro-2,3-dihydro-8-methyl-6-propylergoline, and combinations thereof.

7. The method of claim 1, wherein the subject is suffering from an eating disorder.

8. The method of claim 7, wherein the subject overeats.

9. The method of claim 8, wherein the subject is observed to lose weight.

10. The method of claim 7, wherein the subject undereats.

11. The method of claim 1 in which the at least one symptom of stress is increased blood sugar in the diabetic patient, fatigue, insomnia, high blood pressure, headaches, digestive changes, neck pain, back ache, tension, increased worry, anger, reclusiveness, confusion, pessimism, increased irritability, inability to concentrate, decreased vigor, inability to perform at ones previous level, overeating, undereating, sadness, impairment of self-esteem, or combinations thereof.

12. The method of claim 4 wherein the compound is administered in combination with a serotonergic agent and wherein the serotonergic agent is ergolide mesylate, pergolide mesylate, buspirone, d,1-fenfluramine, dexfenfluramine, tryptophan, lithium, chlorimipramine, cyanimipramine, fluoxetine, paroxetine, fluvoxamine, citalopram, femoxitine, cianopramine, sertraline, sibutramine, venlafaxine or combinations thereof.

13. A method of treating a human subject suffering from or experiencing stress and exhibiting at least one symptom thereof comprising administering to said subject an effective amount of tryptophan, 5-hydroxytryptophan, or a pharmaceutically acceptable salt thereof.

14. The method of claim 13 in which L-tryptophan, L-5hydroxytryptophan, or a pharmaceutically acceptable salt thereof is administered.

15. The method of claim 13, wherein said compound is administered at a dose ranging from about 20 mg to about 4 g/day.

16. The method of claim 15, wherein said compound is administered at a dose ranging from about 50 mg to about 1 g/day.

17. The method of claim 16, wherein said compound is administered at a dose ranging from about 50 mg to about 400 mg/day.

18. The method of claim 17, wherein said compound is administered at a dose ranging from about 80 mg to about 150 mg/day.

19. The method of claim 13, in which the compound is administered in combination with a stimulant of serotonin synthesis.

20. The method of claim 19, in which the stimulant of serotonin synthesis is selected from the group consisting of vitamin B1, vitamin B3, vitamin B6, biotin, 5-adenosylmethionine, folic acid, ascorbic acid, magnesium, coenzyme Q10, piracetam and combinations thereof.

21. The method of claim 13, in which the compound is administered in combination with a serotonergic drug that acts as a serotonin agonist.

22. The method of claim 14, wherein the compound is administered in combination-with a serotonergic agent, and wherein the serotonergic agent is ergolide mesylate, pergolide mesylate, buspirone, d,1-fenfluramine, dexfenfluramine, tryptophan, lithium, chlorimipramine, cyanimipramine, fluoxetine, paroxetine, fluvoxamine, citalopram, femoxitine, cianopramine, sertraline, sibutramine, venlafaxine or combinations thereof.

23. The method of claim 13, in which the compound is administered as a food-based preparation, functional food, dietary supplement, dietary insulin-releasing carbohydrate or nutraceutical.

24. The method of claim 13, wherein said compound is administered by a means selected from the group consisting of oral, parenteral, buccal, sublingual and rectal administration.

25. The method of claim 13, in which the at least one symptom of stress is increased blood sugar in the diabetic patient, fatigue, insomnia, high blood pressure, headaches, digestive changes, neck pain, back ache, tension, increased worry, anger, reclusiveness, confusion, pessimism, increased irritability, inability to concentrate, decreased vigor, inability to perform at ones previous level, overeating, undereating, sadness, impairment of self-esteem, or combinations thereof.

26. The method of claim 13, wherein the compound is derived from a plant, a component or a product thereof.

27. The method of claim 26, wherein the component or product of the plant is selected from the group consisting of root, tuber, rind, peel, bark, seed, fruit, bulb, flower, rhizome, leaf, stem, oil, shell, capsule, twig, resin, extract, bean, and combinations thereof.

28. The method of claim 13, wherein the compound is present in a plant, a component or a product thereof, wherein said administration is effected by the digestion of a sufficient quantity of said plant, component, or product thereof.

* * * * *

US006579899C1

(12) EX PARTE REEXAMINATION CERTIFICATE (10893rd)
United States Patent
Wurtman et al.

(10) Number: US 6,579,899 C1
(45) Certificate Issued: Jun. 24, 2016

(54) COMPOSITION FOR TREATMENT OF STRESS

(75) Inventors: Judith J. Wurtman, Boston, MA (US); Richard J. Wurtman, Boston, MA (US)

(73) Assignee: MASSACHUSETTS INSTITUTE OF TECHNOLOGY, Cambridge, MA (US)

Reexamination Request:
No. 90/013,191, Apr. 24, 2014

Reexamination Certificate for:
Patent No.: 6,579,899
Issued: Jun. 17, 2003
Appl. No.: 09/492,110
Filed: Jan. 27, 2000

Related U.S. Application Data

(63) Continuation-in-part of application No. 09/354,738, filed on Jul. 16, 1999, now abandoned.

(60) Provisional application No. 60/093,013, filed on Jul. 16, 1998.

(51) Int. Cl.
A61K 33/00 (2006.01)
A61K 31/138 (2006.01)
A61K 31/135 (2006.01)
A61K 45/00 (2006.01)
A61K 31/00 (2006.01)
A61K 31/15 (2006.01)
A61K 45/06 (2006.01)
A61K 31/137 (2006.01)
A61K 31/403 (2006.01)
A61K 31/4045 (2006.01)
A61K 31/405 (2006.01)
A61K 31/496 (2006.01)
A61K 31/497 (2006.01)
A61K 38/00 (2006.01)

(52) U.S. Cl.
CPC .............. *A61K 45/06* (2013.01); *A61K 31/00* (2013.01); *A61K 31/135* (2013.01); *A61K 31/137* (2013.01); *A61K 31/138* (2013.01); *A61K 31/15* (2013.01); *A61K 31/403* (2013.01); *A61K 31/405* (2013.01); *A61K 31/4045* (2013.01); *A61K 31/496* (2013.01); *A61K 31/497* (2013.01); *A61K 33/00* (2013.01); *A61K 38/00* (2013.01)

(58) Field of Classification Search
None
See application file for complete search history.

(56) References Cited

To view the complete listing of prior art documents cited during the proceeding for Reexamination Control Number 90/013,191, please refer to the USPTO's public Patent Application Information Retrieval (PAIR) system under the Display References tab.

*Primary Examiner* — Bruce Campell

(57) ABSTRACT

A method of treating stress in a patient showing stress related symptoms is disclosed, where the method comprises administering to the patient an effective amount of a serotoninergic drug or prodrug. Specific examples of such drugs are described, and include, among others, tryptophan or 5-hydroxytryptophan, or their salts.

EX PARTE REEXAMINATION CERTIFICATE

THE PATENT IS HEREBY AMENDED AS INDICATED BELOW.

AS A RESULT OF REEXAMINATION, IT HAS BEEN DETERMINED THAT:

Claims 1-28 are cancelled.

* * * * *